United States Patent [19]

Baker, Jr. et al.

[11] Patent Number: 4,964,407
[45] Date of Patent: Oct. 23, 1990

[54] METHOD AND APPARATUS FOR ASSURING PACER PROGRAMMING IS COMPATIBLE WITH THE LEAD

[75] Inventors: Ross G. Baker, Jr., Houston; Joseph W. Vandegriff, Freeport, both of Tex.

[73] Assignee: Intermedics, Inc., Angleton, Tex.

[21] Appl. No.: 237,719

[22] Filed: Aug. 29, 1988

[51] Int. Cl.⁵ .................................................. A61N 1/00
[52] U.S. Cl. ........................ 128/419 PG; 128/419 P; 128/419 PT
[58] Field of Search ............ 128/419 T, 419 P, 419 D, 128/419 PG

[56] References Cited

U.S. PATENT DOCUMENTS

| | | | |
|---|---|---|---|
| 4,532,931 | 8/1985 | Mills | 128/419 PG |
| 4,549,548 | 10/1985 | Wittkampf et al. | 128/419 PG |
| 4,558,702 | 12/1985 | Barreras et al. | 128/419 PG |
| 4,628,934 | 12/1986 | Pohndorf et al. | 128/419 PG |
| 4,658,831 | 4/1987 | Reinhard et al. | 128/419 PT |

Primary Examiner—Francis Jaworski
Assistant Examiner—George Manuel
Attorney, Agent, or Firm—John R. Merkling

[57] ABSTRACT

A series of test signals are generated by a microprocessor of a pacemaker to determine whether a bipolar or unipolar lead is attached to an implanted cardiac pacemaker restricting programming of said pacemaker to only an unipolar pacing mode unless the presence of an operational bipolar lead is detected. Detection is accomplished by generating a series of low frequency high impedance pulses, applying them to lead contacts and sensing a return signal. If a return signal is detected, then that indicates either a unipolar lead is connected to the pacemaker or that the ring conductor of a bipolar lead is open and bipolar pacing must be inhibited.

27 Claims, 1 Drawing Sheet

METHOD AND APPARATUS FOR ASSURING PACER PROGRAMMING IS COMPATIBLE WITH THE LEAD

BACKGROUND OF THE INVENTION

1. The Field of the Invention

The present invention relates to a method and apparatus for assuring that a pacemaker is properly programmed so that bipolar operation will not be enabled on an implanted unipolar lead and thereby cause loss of capture.

2. Prior Art

The typical implanted cardiac pacemaker operates by supplying missing stimulation pulses on a pacing lead attached to the heart. The so called "R" wave can be sensed by a lead in the ventricle, which lead can be used for purposes of pacing. An additional lead can contact the atrium to sense the "P" wave, if desired. In programmable pacemakers, the fixed rate at which the pulse generator will produce pulses may be selected from among a variety of optional rates, for example, from forty to one hundred beats per minute. It is desirable to have as many rates available as is practical for two reasons. First, it enhances the physician's ability to match the pacemaker to the patient so as to avoid angina and to coordinate the fixed rate with the patient's normal sinus rhythm. Second, the higher the rate, the shorter the lifetime of the pacemaker's battery. By the same token, it is desirable to have a number of different pulse intensities available for selection. Pulse intensity is programmed either by adjusting pulse width or pulse amplitude. It is generally desirable to minimize the pulse intensity to conserve power. The stimulation output of the pulse generator is applied to the heart via two electrodes, namely, a cathode and an anode. Typically the cathode for ventricle pacing is placed adjacent to the tip of an elongated insulated pacing lead which extends pervenously into the right ventricle of the heart. The electrical return path of the anode can be achieved in two different ways. The case of the pulse generator can be used as the anode. In this system, since only one electrode is located at the end of the pacemaker lead, the lead is called an "unipolar" lead. In the other system, the anode is located near the tip of the pacemaker lead displaced and insulatively separated from cathode, which lead is referred to as a "bipolar" lead.

In the past, cardiac pacemakers and pacing leads were available in either unipolar or bipolar configurations and the anode location was irreversibly selected at implantation. If a unipolar lead was implanted and it was determined that sensing could be more reliably obtained with a bipolar lead, or if there were muscular twitching in the vicinity of the pulse generator, the patient had to undergo a further operation to replace both the lead and the pulse generator. Attachment of an unipolar lead to a pacemaker having bipolar operational capability would leave a ring electrode contact unconnected. This condition can be sensed. A similar situation would occur should the ring portion of a bipolar lead develop an open circuit.

A more recent trend has been to provide programmable pacemakers which can be programmed for either unipolar or bipolar operation. There are generally four conditions which can be programmed, namely: unipolar sensing with unipolar pacing; unipolar sensing with bipolar pacing; bipolar sensing with unipolar pacing; and bipolar sensing with bipolar pacing. However, there remains the problem of assuring that the pacemaker will not be programmed for bipolar operation when, in fact, a unipolar lead is implanted and attached to the pacemaker.

The present invention constitutes a method and apparatus for assuring that, at the time of reprogramming an implanted pacemaker, only a program compatible with the type and condition of the implanted lead will be enabled. Normally, a pacemaker capable of bipolar operation is initially programmed for unipolar operation. After implantation, it is necessary to assure there is a functional bipolar lead connected to the pacemaker before initiating a bipolar program. The present invention generates a test signal in a logic and control circuit and passes the signal through an impedance to the electrodes. A sensing amplifier detects the presence of noise, which is either the injected noise signal or actual noise of a fairly high intensity. If the sensing amplifier does detect a signal, and the patient is not in a high noise field, this indicates that a unipolar condition probably exists, either because a unipolar lead was implanted or an implanted bipolar lead is not fully operational, and only unipolar pacing should be programmed.

The present invention teaches programming to a pacing and sensing mode in which a high impedance test signal is applied to a sensing node that will be high impedance (with respect to pacemaker ground $V_{DD}$) if an improper or inoperative electrode for the desired program is connected to the pacemaker. A test signal can be selected from any one of a number of signals including, but not restricted to, signals similar to noise with a requirement that the number of such signals exceed a predetermined minimum number in order to make a determination of the lead configuration. The signal would preferably be generated from a master micro-circuit of the pacemaker. It would also be possible to use clock pulses as a signal source with the additional requirement that the clock pulses be of sufficient amplitude and periodicity as to be readily detectable.

The normal sequence of events is to implant the lead and the pacemaker into the patient, monitor the patient's condition, and then reprogram the pacemaker at later times, as required by the patient's changed condition, by non-invasively transferring parameter value data from an external device, called the programmer, to the pacemaker implanted in the patient's body. A number of programming systems have been successfully employed in commercially available cardiac pacemakers, including magnetic programming and radio frequency programming, to reprogram an implanted pacemaker. Pacemakers are usually initially programmed by the manufacturer to a unipolar sensing and pacing condition. There are programming sequences which are followed when changing from this initial condition. For example, when going to bipolar operation, the present invention goes through an intermediate step of bipolar sensing with unipolar pacing to ensure capture during the test. There is the possibility, due to the time between implanting and the time of reprogramming, that there may be an oversight as to the exact nature of the lead which has been implanted in the patient. There also is the possibility of the ring portion of a bipolar lead becoming open after implantation. One of the problems addressed by the present invention is assuring that this reprogramming is compatible with the type/condition of the lead which is implanted.

SUMMARY OF THE INVENTION

The present invention is a method and apparatus which will prevent the improper programming of a cardiac pacemaker to assure that the programming will be compatible with the type and condition of lead which is implanted and connected to the pacemaker.

The method of the present invention comprises the steps of introducing a high-impedance noise test signal into a sensing node which will be high impedance if a bipolar lead is not present and/or is not properly functioning. If a bipolar lead is attached to the pacemaker, and both electrodes are in contact with body fluids, the test signal will be significantly attenuated with the absence of a sensed signal indicating the presence of a properly functioning bipolar lead. If this test signal is sensed, then unipolar pacing is maintained. The high impedance noise test signal being sensed or not indicates whether or not body impedance is in the circuitry, as it would be for bipolar operation. If the ring electrode is not connected, as would be the case for a unipolar lead or open ring contact, then the pacemaker is maintained in a unipolar pacing condition. The frequency range for the test signal is preferably in the 5-200 Hz range, which is low enough for a sense amplifier to detect. The test signals could be generated by a number of sources.

The apparatus of the present invention is a modification of an existing microprocessor circuit which allows detection of a sense signal.

BRIEF DESCRIPTION OF THE DRAWINGS

The present invention will now be described by way of example with reference to the accompanying drawings in which.

DETAILS OF THE PREFERRED EMBODIMENT

Figure 1:
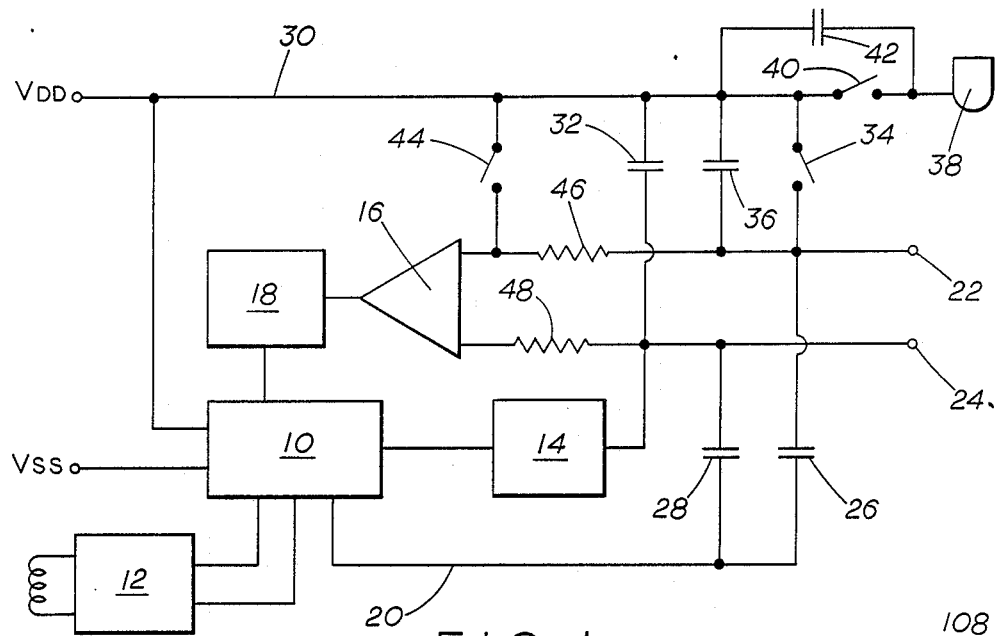
FIG. 1 is a block level diagram illustrating the principle of the present invention with a single chamber programmable pacemaker.
Figure 2:
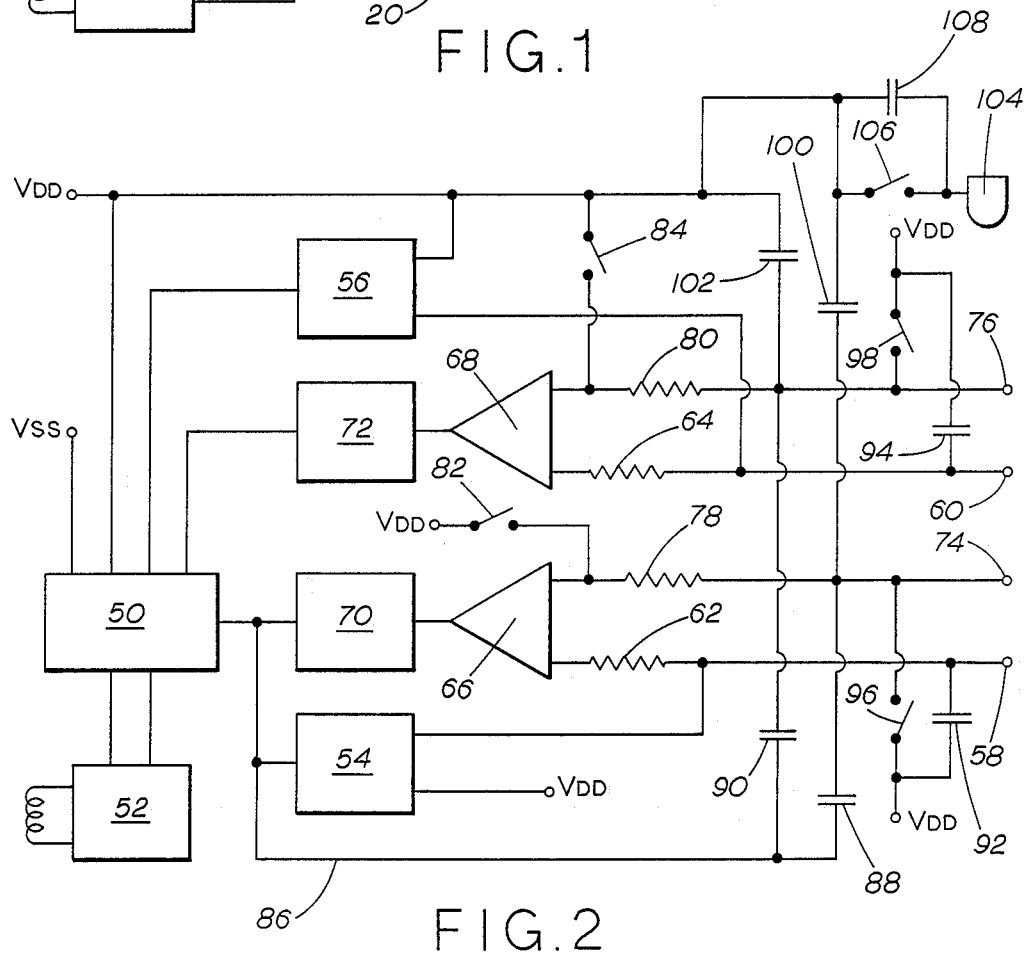
FIG. 2 is a similar block level diagram illustrating the principle of the present invention with a dual chamber programmable pacemaker.

Turning now to the Figures, only those portions of a conventional programmable pacemaker circuitry which are necessary for an understanding of the present invention have been illustrated. FIG. 1 shows circuitry for a single chamber pacemaker and FIG. 2 shows circuitry for a dual chamber pacemaker which, in effect, has double or duplicate circuitry of the single chamber embodiment.

The single chamber pacemaker has a logic and control microcircuit 10 connected to a communication circuit 12 for non-invasively programming the pacemaker. An output circuit 14 is connected between the logic and control circuit 10 and cathode contact 24. A sense amplifier and filter circuit 16 is connected to the logic and control circuit 10 through a threshold detection circuit 18. A test signal line 20 leads from the logic and control circuit 10 to the anode (ring) contact 22 and the cathode (tip) contact 24 through capacitors 26, 28, respectively. The cathode contact 24 is connected to system ground 30 ($V_{DD}$) through capacitor 32 while the anode contact 22 is connected to system ground 30 through switch 34 which has capacitor 36 connected parallel thereto. The pacemaker can 38 is connected to system ground 30 by parallel connected switch 40 and capacitor 42. Switch 44 connects one input to the amplifier and filtering circuit 16 to ground 30. The anode contact 22 and cathode contact 24 are connected to the inputs of the amplifier and filtering circuit 16 through resistors 46 and 48, respectively.

It should be noted here that the switches have been shown as single pole single throw mechanical switches for the sake of convenience only. In an actual embodiment these switches would be electronic switches formed in integrated micro-chip circuits of the pacemaker.

Capacitors 32, 36 and 42 provide electromagnetic interference [EMI] protection for the circuit. The capacitance of capacitors 26 and 28, in combination with the capacitance of these EMI capacitors, is chosen so that the injected test signal is attenuated but still sensible when no bipolar lead is present.

In the single chamber embodiment of FIG. 1, when switch 34 is open and switches 40 and 44 closed, the pacemaker is programmed for unipolar pacing and sensing. When switch 34 is closed and switches 40 and 44 opened, then the pacemaker is programmed for bipolar pacing and sensing. When switch 34 is open, switch 40 closed and switch 44 open, the pacer is programmed for unipolar pacing and bipolar sensing. When switch 34 is open and switches 40 and 44 are closed prior to pace, the pacer is initially programmed for unipolar pacing and sensing but during pacing, and until 12 msec after pacing, switch 40 opens while switches 34 and 44 are closed to program for bipolar pacing. This achieves bipolar pacing with unipolar sensing.

The subject invention operates by injecting a noise signal on test line 20. If an operational bipolar lead is connected to the pacemaker, then the signal would be attenuated and not detected by circuit 18. However, if the injected noise signal is detected, this means either the lead is unipolar or is a malfunctioning bipolar lead, generally meaning the ring electrode is open. If the tip electrode of a bipolar lead was open, then the lead would be totally non-functional and non-operational in either mode. A similar response, namely, detected signal, could occur should the patient be in a high noise field. Suitable precautions would have to be taken to avoid having a high noise field present during reprogramming of the pacemaker. The normal reaction of a pacemaker upon detecting noise is to go into an asynchronous pacing mode. A programmer reading noise detection by the pacemaker will try several times to program a bipolar mode and then go to an unipolar mode.

The subject method involves the step of introducing a high impedance noise test signal from a programmable microchip onto a ring electrode of a bipolar contact. This test signal can be selected from any of a variety of test signals, including but not restricted to, timing pulses and square waves. The only significance of the test signal is that it must be in a frequency range low enough to be detected by a sensing amplifier, for example, a 2.5 volt square wave test signal connected to the ring contact through a 100 mega ohm resistor, which could also be capacitively blocked. The input amplifier (given an sense impedance of 100 mega ohms) will see a 1.25 volt square wave, which can easily be detected. If a lead is attached to the pacemaker and in contact with body fluids, the test signal will be significantly attenuated and not detected thus indicating the presence of a functional bipolar lead. Given a worse case lead impedance of 2 K ohms, the test signal seen by the amplifier will be 50 microvolts, which will not be sensed at any setting. If this test signal is sensed a sufficient number of times (and enough test signals must be generated to distinguish these impulses from valid detected sensing signals) unipolar pacing must be maintained. If both sensing and pacing are separately programmable, bipolar sensing should be tried before bipolar pacing is allowed. A test algorithm in a pacemaker would provide for bipolar lead detection.

The dual chamber embodiment of FIG. 2 differs from the single chamber embodiment by doubling some of the components. In this embodiment the logic and control circuit 50 is connected to a communicating circuit 52 for non-invasively programming the pacemaker. First and second output circuits 54, 56 are connected between the logic and control circuit 50 and the respective ventricle cathode 58 and atrium cathode 60. Each is also connected through a resistor 62, 64, an amplifier and filtering circuit 66, 68, a threshold detection circuit 70, 72 to the logic and 68 control circuit 50. The anode contacts 74, 76 are connected to the second inputs of the amplifier and filter circuits 66, 68 through resistors 78, 80. Both of these inputs are connected to system ground through switches 82, 84. A test signal output line 86 from the logic and control circuit is connected through capacitors 88, 90 to anode contacts 74, 76, respectively. Each cathode contact 58, 60 is connected to system ground through capacitor 92, 94 and the anode contacts 74, 76 are switched to system ground by switches 96, 98. The anode contacts are connected to system ground through capacitors 100, 102. The pacer can 104 is connected to system ground through a parallel circuit of switch 106 and capacitor 108.

In this dual chamber embodiment, capacitors 92, 94, 100, 102 and 108 are for EMI protection.

It has been previously mentioned that the reprogramming of the implanted pacemaker would be by an external programmer. An example of this type of commercially available device the Rx 2000 programmer manufactured and sold by Intermedics, Inc. of Angleton, Tex.

The present invention may be embodied in other configurations and forms without departing from the spirit or essential characteristics thereof. All embodiments which come within the meaning of equivalency are therefore to be embraced herein.

We claim:

1. A circuit for recognizing a functional bipolar lead attached to an implantable cardiac pacemaker capable of bipolar and unipolar operation, the pacemaker comprising a pulse generator, an indifferent electrode, an anode lead connector and a cathode lead connector, the circuit comprising:
    means for generating a test signal;
    impedance means connecting said signal generating means and said anode lead connector;
    means for providing a low impedance path connecting the anode lead connector to the ground potential through said functional bipolar lead if said functional bipolar lead is connected to said cardiac pacemaker, the path passing through a portion of a patient's body;
    means for sensing a level of the test signal at the anode lead connector; and
    means for disabling bipolar pacing of the pacemaker if the test signal at the anode lead connector exceeds a predetermined value.

2. The circuit according to claim 1 wherein the means for providing the low impedance path further comprise the indifferent electrode.

3. The circuit according to claim 1 wherein the signal generating means further comprise means for generating a series of test signals, and wherein the bipolar pacing disabling means further comprise means for disabling bipolar pacing of the pacemaker if the test signal at the anode lead connector exceeds the predetermined value for a predetermined number of test signals.

4. The circuit according to claim 1 wherein the impedance means comprise a capacitor.

5. The circuit according to claim 1 wherein the means for disabling the bipolar pacing further comprise means for enabling unipolar pacing of the pacemaker.

6. A circuit for recognizing a functional bipolar lead attached to an implantable cardiac pacemaker capable of bipolar and unipolar operation, the pacemaker comprising a pulse generator and at least one lead connection comprising an anode and a cathode connector, said circuit comprising:
    means for generating a test signal;
    impedance means connecting said signal generating means and said cathode connector;
    a low impedance path connecting said anode connector to the ground potential;
    means for providing a low impedance path connecting the cathode connector to the anode connector through said functional bipolar lead if said functional bipolar lead is connected to said cardiac pacemaker, the path adapted for passing through a portion of a patient's body;
    means for disabling bipolar pacing of the pacemaker if the test signal at the cathode connector exceeds a predetermined value.

7. The circuit according to claim 6 wherein the sensing means comprise means for sensing the difference between the level of the test signal at the cathode connector and a level of the test signal at the anode connector, and wherein the disabling means comprise means for disabling bipolar pacing of the pacemaker if the difference between the level of the test signal at the cathode connector and the level of the test signal at the anode connector exceeds the predetermined value.

8. The circuit according to claim 6 wherein the signal generating means further comprise means for generating a series of test signals, and wherein the bipolar pacing disabling means further comprise means for disabling bipolar pacing of the pacemaker if the level of the test signal at the cathode connector exceeds the predetermined value for a predetermined number of test signals.

9. The circuit according to claim wherein the impedance means comprise a capacitor.

10. The circuit according to claim 6 wherein the means for disabling the bipolar pacing further comprise means for enabling unipolar pacing of the pacemaker.

11. A method for recognizing a functional bipolar lead attached to an implantable cardiac pacemaker capable of bipolar and unipolar operation, the method comprising:
    generating a test signal;
    passing the test signal through an impedance to an anode connector in the pacemaker;
    providing a low impedance path between the anode connector and the ground potential through portion of a patient's body and through a functional anode of a bipolar lead if said bipolar lead is connected to said cardiac pacemaker,
    sensing a level of the test signal at the anode lead connector; and disabling bipolar pacing of the pacing if the level of the test signal at the anode lead connector exceeds a predetermined value.

12. The method according to claim 11 wherein the step of disabling the bipolar pacing further comprises communicating a status of the sensed test signal to an external pacemaker programming device and programming the pacemaker for unipolar operation.

13. The method according to claim 11 wherein the step of generating the test signal comprises generating a series of test signals and wherein the disabling step comprises disabling the bipolar pacing of the pacemaker if the level of the test signal at the anode connector exceeds the predetermined value for a predetermined number of test signals.

14. The method according to claim 11 wherein the step of disabling bipolar pacing further comprises enabling unipolar pacing of the pacemaker.

15. A method for recognizing a functional bipolar lead attached to an implantable cardiac pacemaker capable of bipolar and unipolar operation comprising:
generating a test signal;
conducting the test signal through an impedance to a cathode connector in electrical communication with a cathode of a lead;
connecting an anode connector through a low impedance path to the ground potential;
providing a low impedance path connecting the cathode connector to the anode connector through a portion of a patient's body and through a functional bipolar lead if said functional bipolar lead is connected to said cardiac pacemaker;
sensing a level of the test signal at the cathode connector; and
disabling bipolar pacing of the pacemaker if the level of the test signal at the cathode connector exceeds a predetermined value;
wherein the step of disabling bipolar pacing further comprises communicating a status of the sensed test signal to an external pacemaker programming device and programming the pacemaker for unipolar operation.

16. The method according to claim 15 wherein the signal generating step comprises generating a series of test signals and of the pacemaker if the level of the test signal at the cathode connector exceeds the predetermined value for a predetermined number of test signals.

17. The method according to claim 15 wherein the step of disabling bipolar pacing further comprises enabling unipolar pacing of the pacemaker.

18. An implantable cardiac pacemaker capable of bipolar and unipolar operation, comprising
a pulse generator;
an indifferent electrode connected to the pulse generator;
an anode lead connector connected to the pulse generator;
a cathode lead connector connected to the pulse generator;
means for generating a test signal for recognition of a functional bipolar lead;
impedance means connecting said signal generating means and said anode lead connector;
means for providing a low impedance path connecting the anode lead connector to the ground potential through said functional bipolar lead if said functional bipolar lead is connected to said cardiac pacemaker, the path adapted for passing through a portion of a patient's body;
means for sensing a level of the test signal at the anode lead connector; and
means for disabling bipolar pacing of the pacemaker if the test signal at the anode lead connector exceeds a predetermined value.

19. The implantable cardiac pacemaker according to claim 18 wherein the means for providing the low impedance path further comprise the indifferent electrode.

20. The implantable cardiac pacemaker according to claim 18 wherein the signal generating means further comprise means for generating a series of test signals, and wherein the bipolar pacing disabling means further comprise means for disabling bipolar pacing of the pacemaker if the test signal at the anode lead connector exceeds the predetermined value for a predetermined number of test signals.

21. The implantable cardiac pacemaker according to claim 18 wherein the impedance means comprise a capacitor.

22. The implantable cardiac pacemaker according to claim 18 wherein the means for disabling the bipolar pacing further comprise means for enabling unipolar pacing of the pacemaker/

23. An implantable cardiac pacemaker capable of bipolar and unipolar operation comprising
a pulse generator;
at least one lead connection in electrical communication with the pulse generator, said lead connection comprising an anode connector and a cathode connector;
means for generating a lead test signal;
impedance means connecting said signal generating means and said cathode connector;
a low impedance path connecting said anode connector to the ground potential;
means for providing a low impedance path connecting the cathode connector to the anode connector through a functional bipolar lead if said functional bipolar lead is connected to said cardiac pacemaker, the path adapted for passing through a portion of a patient's body;
means for sensing a level of the test signal at the cathode connector; and
means for disabling bipolar pacing of the pacemaker if the test signal at the cathode connector exceeds a predetermined value.

24. The implantable cardiac pacemaker according to claim 23 wherein the sensing means comprise means for sensing the difference between the level of the test signal at the cathode connector and a level of the test signal at the anode connector, and wherein the disabling means comprise means for disabling bipolar pacing of the pacemaker if the difference between the level of the test signal at the cathode connector and the level of the test signal at the anode connector exceeds the predetermined value.

25. The implantable cardiac pacemaker according to claim 23 wherein the the signal generating means further comprise means for generating a series of test signals, and wherein the bipolar pacing disabling means further comprise means for disabling bipolar pacing of the pacemaker if the level of the test signal at the cathode connector exceeds the predetermined value for a predetermined number of test signals.

26. The implantable cardiac pacemaker according to claim 23 wherein the impedance means comprise a capacitor.

27. The implantable cardiac pacemaker according to claim 23 wherein the means for disabling the bipolar pacing further comprise means for enabling unipolar pacing of the pacemaker.

* * * * *